US008633438B2

(12) United States Patent
Tokita et al.

(10) Patent No.: US 8,633,438 B2
(45) Date of Patent: Jan. 21, 2014

(54) ULTRAFAST ELECTRON DIFFRACTION DEVICE

(75) Inventors: Shigeki Tokita, Uji (JP); Masaki Hashida, Osaka (JP); Shuji Sakabe, Toyono-gun (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/575,619

(22) PCT Filed: Jan. 25, 2011

(86) PCT No.: PCT/JP2011/051350
§ 371 (c)(1),
(2), (4) Date: Jul. 27, 2012

(87) PCT Pub. No.: WO2011/093285
PCT Pub. Date: Aug. 4, 2011

(65) Prior Publication Data
US 2012/0312987 A1  Dec. 13, 2012

(30) Foreign Application Priority Data

Feb. 1, 2010  (JP) ................................ 2010-020723

(51) Int. Cl.
*H01J 37/295* (2006.01)
*H01J 37/04* (2006.01)
(52) U.S. Cl.
USPC ............ 250/305; 250/306; 250/307; 250/311
(58) Field of Classification Search
USPC ......................................... 250/305–307, 311
See application file for complete search history.

(56) References Cited

U.S. PATENT DOCUMENTS

| 4,730,166 | A | * | 3/1988 | Birx et al. ...................... 315/500 |
| 5,130,994 | A | * | 7/1992 | Madey et al. ..................... 372/2 |
| 7,858,951 | B1 | * | 12/2010 | Douglas ................. 250/396 ML |
| 2002/0060521 | A1 | * | 5/2002 | Mako et al. ........................ 315/5 |

OTHER PUBLICATIONS

Harb et al, "Electronically Driven Structure Changes of Si Captured by Femtosecond Electron Diffraction", Physical Review Letters 100, 155504 (2008).*
Kang and Kim, "Femtosecond Electron Beam Bunch Compression by Using an Allpha Magnet and a Chicane Magnet at the PAL Test Linac", Journal of the Korean Physical Society, vol. 44, No. 5, May 2004, pp. 1223-1228.*

(Continued)

*Primary Examiner* — Robert Kim
*Assistant Examiner* — David E Smith
(74) *Attorney, Agent, or Firm* — Oliff & Berridge, PLC (57) ABSTRACT

An ultrafast electron diffraction device for irradiating a sample with a bunch of electrons in an ultrashort pulse in order to perform an ultrafast analysis of the sample. The ultrafast electron diffraction device includes: a) a laser emitter for delivering an ultrashort pulse laser having a pulse width of not more than 1 ps onto a target which is a material for generating electrons at an intensity of not less than $10^{17}$ W/cm$^2$; and b) a pulse compressor for rotating, in a magnetostatic field, a bunch of electrons generated from the target onto which the ultrashort pulse laser has been delivered so as to suppress the spread of the bunch of electrons in their traveling direction. The pulse compressor is composed of an entrance-side parallel-plate static magnet, one end of which is placed on the course of the bunch of electrons, and an exit-side parallel-plate static magnet.

9 Claims, 9 Drawing Sheets

(56) References Cited

OTHER PUBLICATIONS

Apr. 19, 2011 Written Opinion of the International Searching Authority issued in International Patent Application No. PCT/JP2011/051350 (with translation).

Apr. 19, 2011 International Search Report issued in International Patent Application No. PCT/JP2011/051350.

Shuji Sakabe et al., "Ultra-fast Electron Diffraction With Electrons Produced by Intense Short Pulse Lasers", Japan Congress on High Speed Imaging and Photonics Ronbunshu, Dec. 10, 2009, pp. 75-77.

Shigeki Tokita et al., "External Electric Field Dependence of the Flourescence of Nitrogen Molecules to Filament Plasma Induced by Ultra-short Laser Pulses", Extended Abstracts, Japan Society of Applied Physics and Related Societies, Mar. 30, 2009, p. 1145.

Shunsuke Inoue et al., "High Definition Measurement for the Space Distribution of Electron Sources Produced by an Intense Short Pulse Laser", Extended Abstracts, Japan Society of Applied Physics, Sep. 8, 2009, p. 1011.

Maher Harb et al., "Electronically Driven Structure Changes of Si Captured by Femtosecond Electron Diffraction", Physical Review Letters, Apr. 18, 2008, Prl. 100, pp. 155504-1 thru 155504-4.

J. Cao et al., "Femtosecond Electron diffraction for Direct Measurement of Ultrafast Atomic Motions", Applied Physics Letters, Aug. 4, 2003, vol. 83, No. 5, pp. 1044-1046.

Christoph T. Hebeisen et. al., "Femtosecond Electron Pulse Characterization Using Laser Ponderomotive Scattering", Optics Letters, Dec. 1, 2006, vol. 31, No. 23, pp. 3517-3519.

\* cited by examiner

ULTRAFAST ELECTRON DIFFRACTION DEVICE

TECHNICAL FIELD

The present invention relates to an ultrafast electron diffraction device for observing a phenomenon on an atomic or molecular level which changes in femtoseconds (i.e. at an ultra-high speed) by using an electron beam of an ultrashort pulse.

BACKGROUND ART

Conventionally, electron microscopes are widely used in the observation of various states on an atomic or molecular level by the electron diffraction method. Recently, a method for observing oscillation of atoms or molecules, their structural changes, or their changes in a chemical reaction in an ultra-short period of time by using an ultrashort (i.e. of a few hundreds femtoseconds) electron beam pulse has been studied. This method is called ultrafast electron diffraction (UED).

Figure 1:
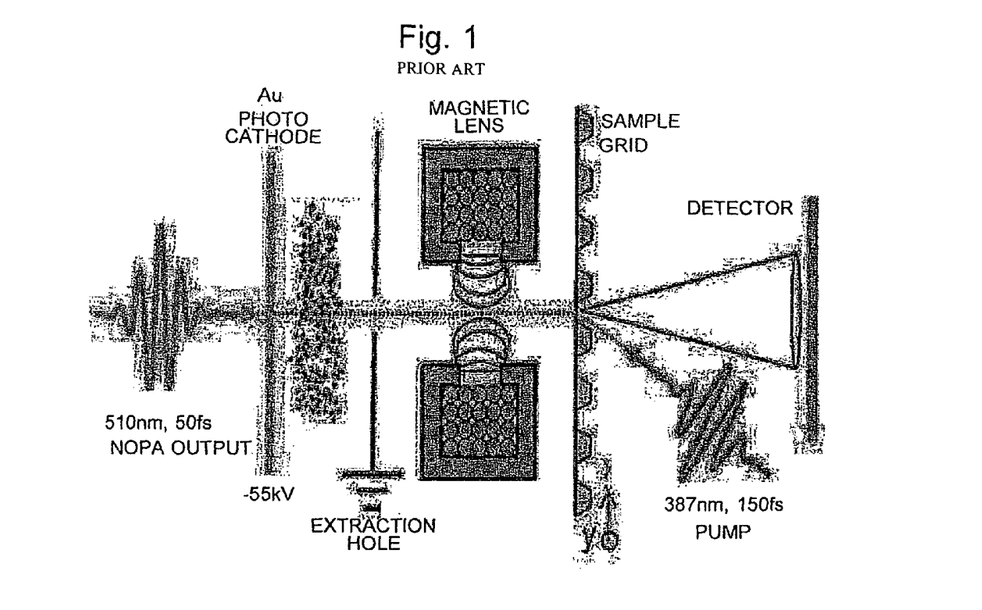
FIG. 1 is a schematic configuration diagram of a conventional ultrafast electron diffraction (UED) device.

Non-Patent Document 1 discloses a UED device which is configured as shown in FIG. 1. In this device, a photocathode (Au) is irradiated with an ultrashort pulse laser at a wavelength of 510 nm and with a pulse width of 50 fs (femtoseconds) to generate a bunch of electrons by the photoelectric effect. The generated bunch of electrons is accelerated by the potential of 55 kV (hereinafter, the accelerated bunch of electrons will be referred to as an electron beam). Subsequently, the bunch of electrons is delivered to the sample on the sample grid by being taken from an extraction hole, dispersed, and then converged in the xy direction (i.e. the direction perpendicular to the traveling direction of the electron beam) by a magnetic lens. A pump light (387 nm, 150 fs) is delivered onto the sample in order to produce a high-speed change in the sample. The electron beam, which is delivered onto the sample after a certain period of time has elapsed since the delivery of the pump light, is diffracted inside the sample by the ordered structure of its atoms and molecules. The diffraction pattern is detected by a detector behind the sample. The ordered structure of the atoms and molecules of the sample can be identified by analyzing the diffraction pattern.

The structure of the sample identified as previously described reflects a moment of a state in which the sample was changing at a high speed (from the point in time of the excitation as a result of the irradiation of the pump light). Repeating such an ultrafast analysis (for multiple shots) while changing the period of time (i.e. delay time) between the irradiation of the pump light and the electron beam can provide the full picture of how the sample changes at high speed.

BACKGROUND ART DOCUMENT

Non-Patent Documents

[Non-Patent Document 1] M. Harb et al., Phys. Rev. Lett., 100, 155504 (2008)
[Non-Patent Document 2] J. Cao, et al., "Femtosecond electron diffraction for direct measurement of ultrafast atomic motions", APPLIED PHYSICS LETTERS, Vol. 83, No. 5 (2003.8.4)

DISCLOSURE OF THE INVENTION

Problem to be Solved by the Invention

In the aforementioned UED device, a bunch of electrons from the target is generated by the photoelectric effect, and therefore it has a very small initial velocity. Since the electrons are collectively accelerated by the electric potential, they are well compressed spatially in their traveling direction just after the electrons are generated. However, before reaching the sample, the bunch of electrons gradually broadens due to the space-charge effect by the Coulomb force among electrons.

Figure 2:
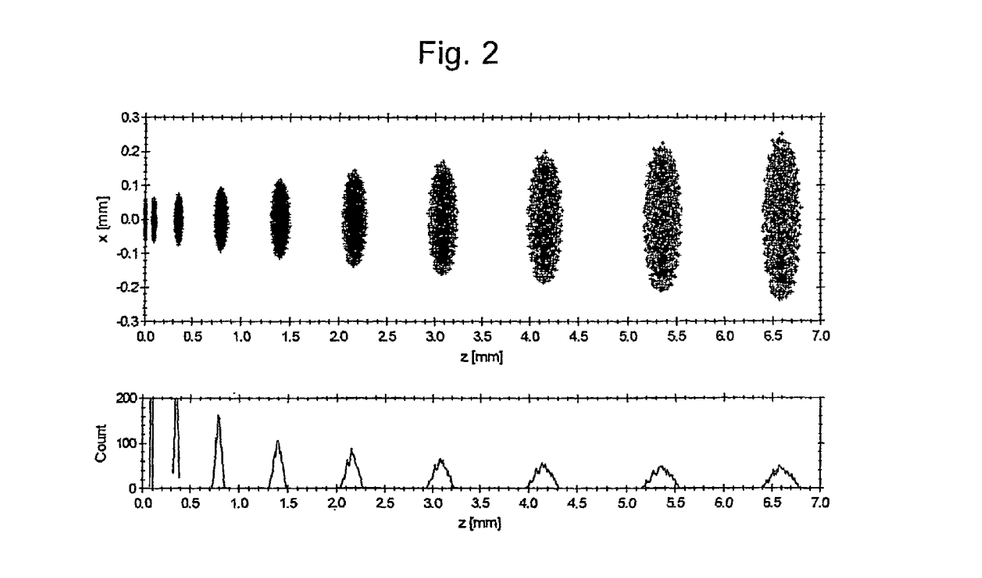
FIG. 2 shows the results of a simulation in which a bunch of electrons spread while flying in a conventional UED device has been computed.

FIG. 2 is a computational result of a simulation showing how a bunch of electrons spreads out in the x-direction (upper graph) and in the z-direction (lower graph). The conditions of the simulation are as follows.

Conditions of the Simulation
Total Electric Charges: 100 fC (number of electrons: $6.2 \times 10^5$)
Accelerating Electric Field: 50 kV/5 mm (10 MV/m)
Spatial Width of the Photocathode: 50 μm (full width at half maximum, Gaussian distribution)
Initial Pulse Width: 50 fs (full width at half maximum, Gaussian distribution)

A problem of the device of FIG. 1 is that, although electrons can be compressed in the xy directions by the magnetic lens, there is no means of preventing them from spreading in the z-direction, which precludes a desired ultrafast diffraction. In particular, in order to obtain a temporal resolution not more than one picosecond (1 ps) in such a device, the total electric charges of a bunch of electrons are required to be approximately 10 fC (femtocoulombs) or less and its electron energy is required to be approximately 50 keV or less. With such a weak electron beam, it is difficult to obtain an image by a single shot that can be adequately analyzable. In addition, such a weak electron beam significantly restricts the objects that can be observed. That is, the kind, thickness, and other factors of a sample are limited.

The problem to be solved by the present invention is to provide an ultrafast electron diffraction device capable of emitting an electron beam which is significantly compressed even in the z-direction (traveling direction) at the point when it is delivered onto a sample.

Means for Solving the Problem

To solve the aforementioned problem, the present invention provides an ultrafast electron diffraction device for irradiating a sample with a bunch of electrons in an ultrashort pulse in order to perform an ultrafast analysis of the sample, including:

a) a laser emitter for delivering an ultrashort pulse laser having a pulse width of not more than 1 ps onto a material for generating electrons (which will be referred to as a "target") at an intensity of not less than $10^{17}$ W/cm²; and b) a pulse compressor for rotating, in a magnetostatic field, a bunch of electrons generated from the target onto which the ultrashort pulse laser has been delivered so as to suppress a spread of the bunch of electrons in their traveling direction.

Based on the same principle, the present invention also provides an ultrafast electron diffraction method, including:

a) a laser emission step for delivering an ultrashort pulse laser having a pulse width of not more than 1 ps onto a target at an intensity of not less than $10^{17}$ W/cm²;

b) a pulse compression step for rotating, in a magnetostatic field, a bunch of electrons generated from the target onto which the ultrashort pulse laser has been delivered so as to suppress a spread of the bunch of electrons in their traveling direction; and c) a step for delivering the bunch of electrons whose spread in the traveling direction has been suppressed onto a sample.

Figure 3:
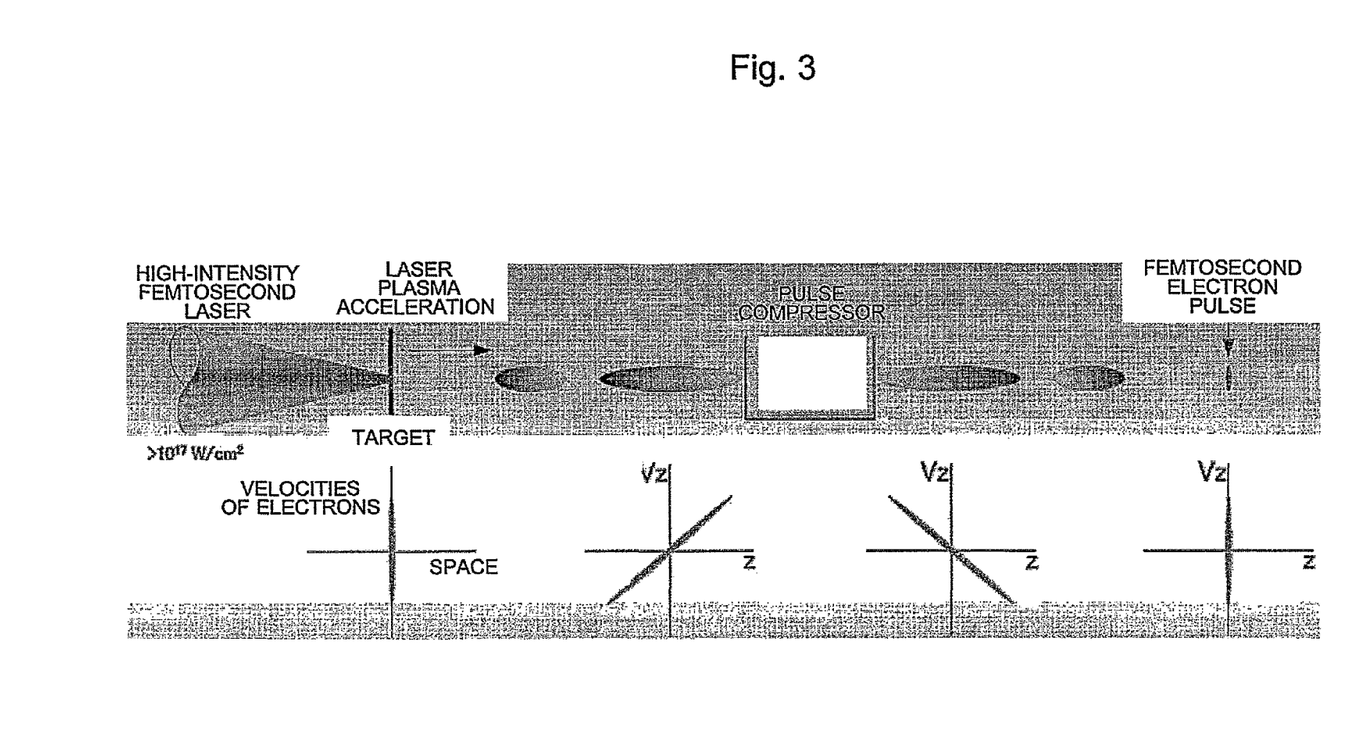
FIG. 3 is a schematic configuration diagram of the ultrafast electron diffraction device according to the present invention.
Figure 4:
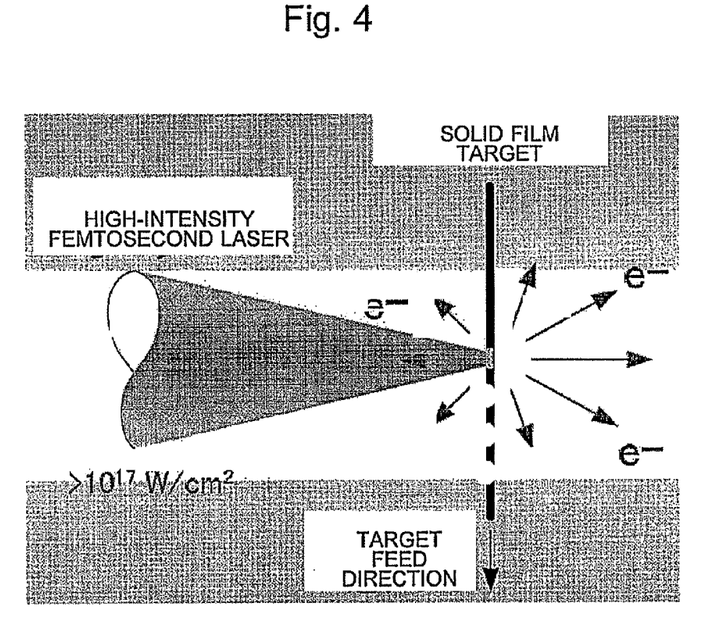
FIG. 4 is a schematic configuration diagram showing how a bunch of electrons is generated in the ultrafast electron diffraction device according to the present invention.

FIG. 3 shows a schematic configuration of the ultrafast electron diffraction device according to the present invention. When a high-intensity femtosecond laser with an intensity of not less than $10^{17}$ W/cm$^2$ is condensed and delivered onto a target, the target is converted into a plasma state. Electrons from the target are accelerated by the Ponderomotive force of the high-intensity femtosecond laser and other causes, so as to be emitted from the target as an ultrashort pulse of a bunch of electrons having a variety of kinetic energies (FIG. 4).

As previously described, the bunch of electrons spreads also in the z-direction as they fly. However, in the ultrafast electron diffraction device according to the present invention, a pulse compressor which is placed in the middle of the course compresses the width of the bunch in its traveling direction (i.e. z-direction), and, furthermore, reverses the positions of high-speed electrons and low-speed electrons. Consequently, it is possible for the pulse width of the bunch of electrons to be at its smallest just as it arrives at the sample. In this manner, an ultrashort pulse can be delivered to the sample.

In the ultrafast electron diffraction device according to the present invention, almost anything can be used as the target, such as metal, a semiconductor, or a macromolecule. In addition to solids, the target may be a liquid or gas. In any case, delivering an ultrashort pulse laser at an intensity of not less than $10^{17}$ W/cm$^2$ generates a bunch of electrons having a large velocity distribution from the target.

The energy of the laser delivered onto the target is adjusted to be not less than $10^{17}$ W/cm$^2$ on the target. Actually, it is preferable to adjust the energy according to the kind, density, and other factors of the target so that the energy of the electrons to be generated is approximately 100 through 500 keV. If the energy of the electrons is higher than this range, a common sample might be damaged, and the scattering cross section of the electrons may be small, which might impede a sufficient diffraction. Of course, a sufficient diffraction will not occur also in the case where the energy of the electrons is lower than that range. However, if a target object is observed with a 1 MeV electron microscope, this method can be used as previously described if electrons of not less than 500 keV are generated by a higher laser intensity.

The pulse compressor can be of any type. In any case, it uses the following principle. While electrons are flying in a magnetostatic field which is perpendicular to their course, they are bent and rotated by the Lorentz force which operates in the direction perpendicular to the course and magnetic field. High energy electrons (i.e. those flying faster) rotate with a larger orbit while flying, whereas low energy electrons (i.e. those flying slower) rotate with a smaller orbit. Therefore, appropriately setting the intensity, distribution, and other factors of the magnetostatic field in accordance with the energy of electrons enables identical positioning of the high-speed electrons and low-speed electrons at the target position. In other words, the spread of a bunch of electrons can be suppressed in its traveling direction on the sample to be irradiated therewith.

Effects of the Invention

With the ultrafast electron diffraction device according to the present invention, an electron beam is compressed in its traveling direction (z-direction) by the pulse compressor which is placed in the middle of its flying course, so as to be delivered onto a sample at an ultra-high speed (i.e. in an ultra-short period of time). This enables an observation of an ultra-fast phenomenon in the sample. Additionally, since an electron beam is not subject to the space-charge effect, it is possible to deliver an electron beam having a sufficient charge amount and energy even in a single shot. This allows an observation with few limitations as to the kind, thickness, and other factors of the sample.

In addition, the ultrafast electron diffraction device according to the present invention does not require an additional unit for accelerating electrons as in conventional devices. Hence, it can operate in a low-vacuum environment, and does not require a high-voltage power supply. That is, the device is simple and can be manufactured at low cost.

BEST MODES FOR CARRYING OUT THE INVENTION

An ultrafast electron diffraction device using a 360° bending magnet, which is an embodiment of the present invention, will be described with reference to FIGS. 5 through 11.

Figure 5:
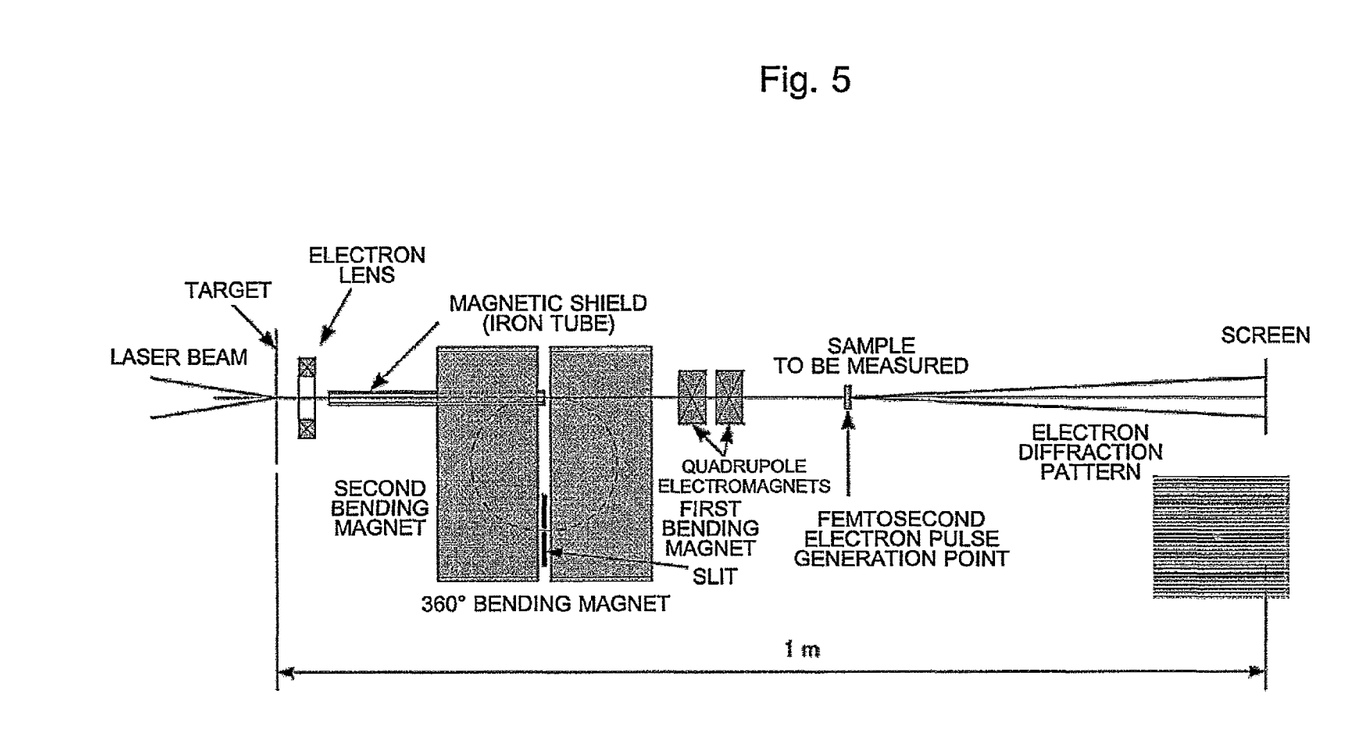
FIG. 5 is a configuration diagram of an ultrafast electron diffraction device according to an embodiment of the present invention.

FIG. 5 is a configuration diagram of an ultrafast electron diffraction device of the present embodiment. A high-energy femtosecond laser pulse (wavelength of 800 nm, pulse width of 130 fs, pulse energy of approximately 70 mJ, and maximum repetition frequency of 10 Hz) generated by a titanium-sapphire laser amplification system was set off-axis. The laser pulse was condensed into a diameter of approximately 5 μm (full width at half maximum) by using a parabolic mirror, and delivered onto a polyethylene membrane target with a thickness of 10 μm. A part of the electron beam generated from the area where the laser was condensed was shaped to have a larger spread angle with an electron lens, which is a permanent magnet, as well as an aperture (not shown) having a diameter of 1 mm which is provided immediately after the electron lens. This electron beam was passed through a 360° bending magnet in order to change the traveling order of high-speed electrons and low-speed electrons so that the electron beam is converged at the measurement position of the sample.

Figure 6:
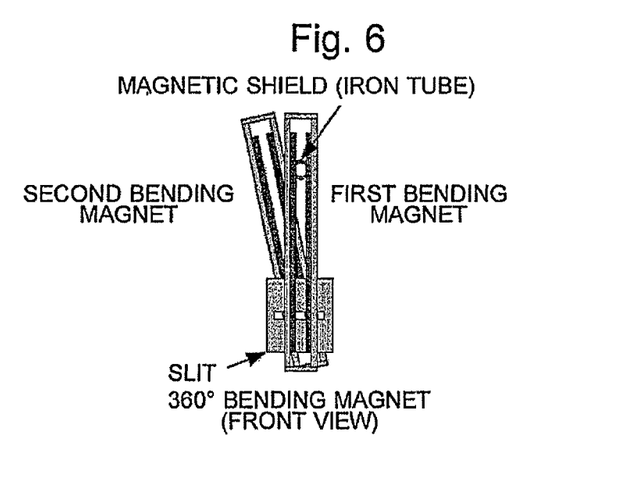
FIG. 6 is a front view of a 360° bending magnet which is used in the ultrafast electron diffraction device of the embodiment.

The 360° bending magnet is composed of two sets of bending magnets which are arranged in the travelling direction of an electron beam. Each set of bending magnets is composed of a pair of rectangular planer magnets which are arranged in parallel and have a pole distance of 3 mm and which generate a uniform magnetic field at a magnetic field intensity of approximately 63 mT. As shown in FIG. 6, these sets of bending magnets are tilted at an angle of 12° to each other. An electron beam is first injected into the first bending magnet which is placed posterior (at the side of the sample to be measured) to a second bending magnet in terms of its traveling direction and is thereby bent at 180°. The electron beam passes through an energy selection slit (with a width of approximately 1 mm), and it is injected into the second bending magnet, where it is further bent at 180° and ejected therefrom. A magnetic shield made of an iron tube is provided on the course of the electron beam so that it will not be affected by the magnetic field of the second bending magnet or any other factors before entering the first bending magnet.

Figure 7:
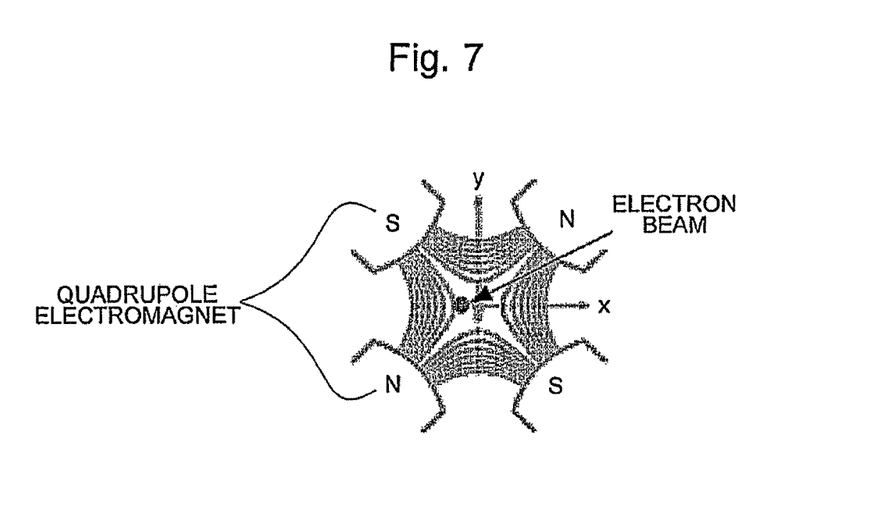
FIG. 7 is a sectional view showing the effects of a quadrupole electromagnet which is used in the ultrafast electron diffraction device of the embodiment.

Two quadrupole electromagnets are placed on the path of the beam which has been bent 360°. The spread-angles in the horizontal and perpendicular directions of the electron beam were adjusted so as to minimize the diameter of the electron beam on the screen by regulating the values of the electric currents of the two quadrupole electromagnets. In addition, the dispersion which occurs in the bending magnets was corrected by displacing the central axis of the quadrupole electromagnets from the beam axis, as shown in FIG. 7.

As a sample to be measured, a 10 nm thick, single crystal (001) thin film of gold was placed on the path of the electron beam which has passed the quadrupole electromagnets. The diameter of the electron beam at the position of the sample was approximately 0.8 mm. The electrons scattered by the sample to be measured are projected onto the fluorescent screen which is placed 413 mm behind the sample. The diffraction pattern formed on the screen was photographed by an electron multiplying charge coupled device (EMCCD) camera.

Figure 8:
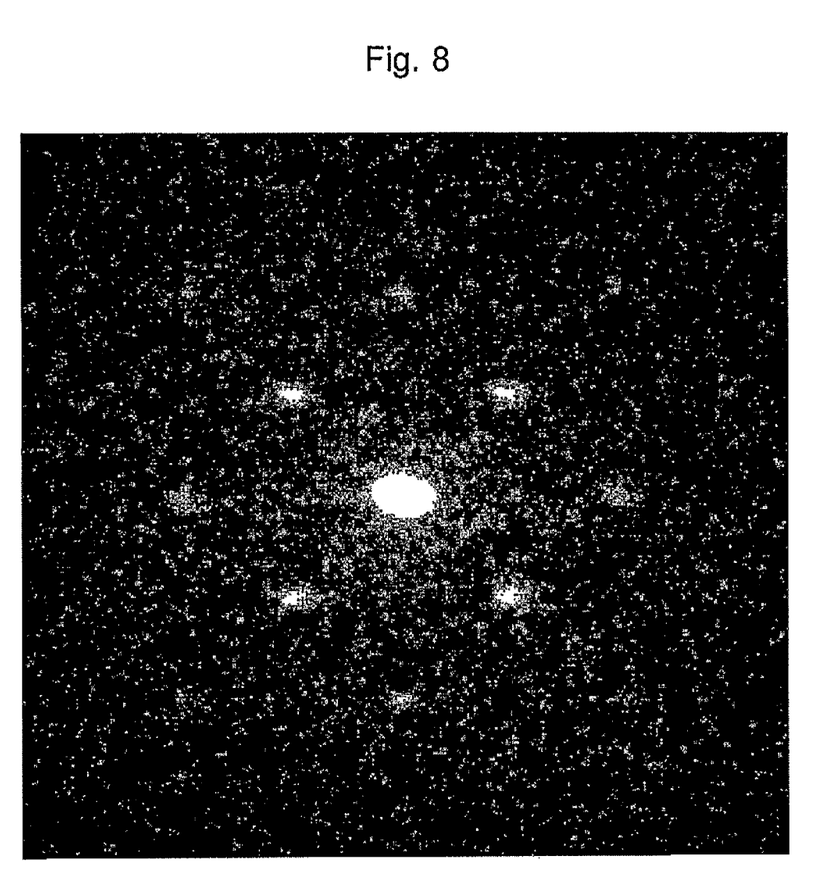
FIG. 8 shows a diffraction pattern obtained by a single shot imaging using the ultrafast electron diffraction device of the embodiment.

FIG. 8 shows a diffraction pattern taken by a single shot. The diffraction spots of (020) and (220) planes are clearly observed, showing that the beam intensity was sufficient for a single shot imaging. Based on the known lattice constant of a single crystal of gold, the energy of the electron beam was computed to be 356 keV.

Figure 9:
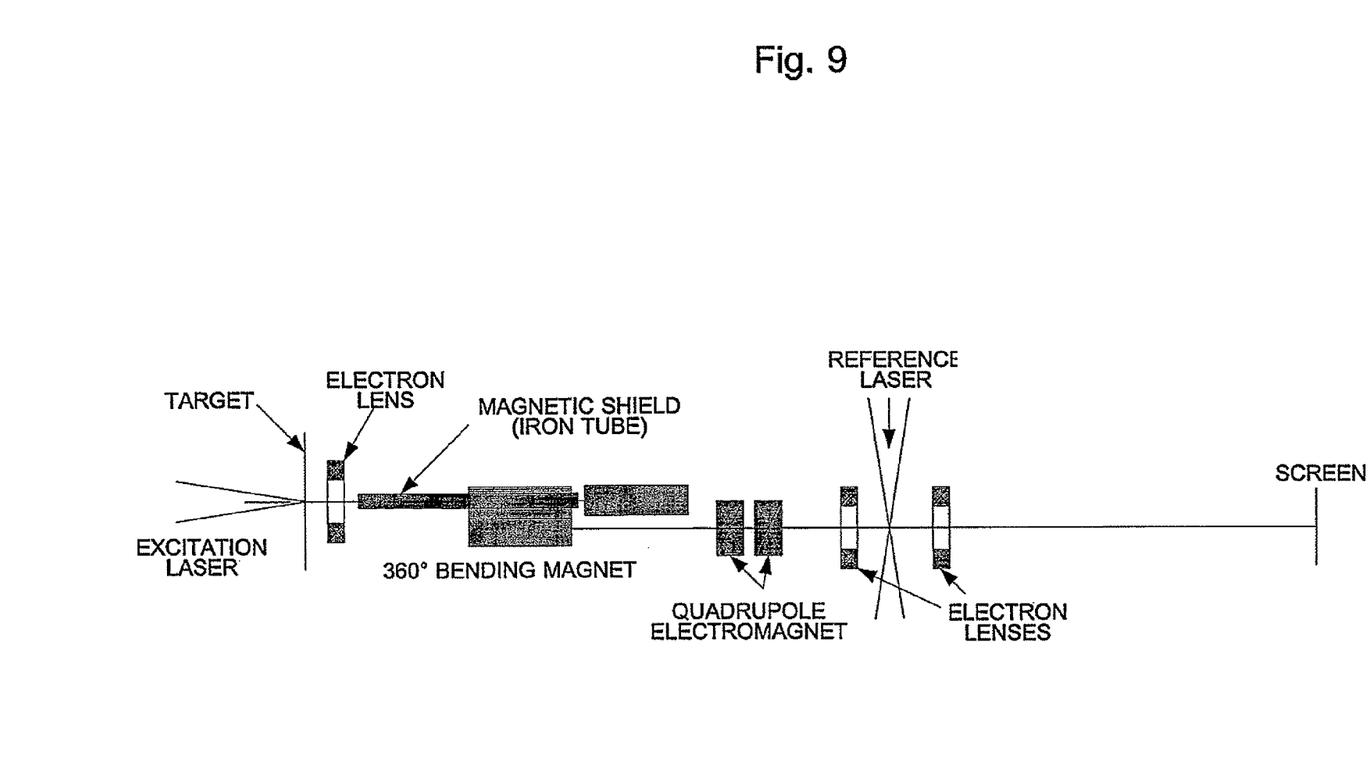
FIG. 9 is a configuration diagram of an apparatus for measuring the time width of an electron pulse that is delivered onto a measurement sample by the aforementioned sample.
Figure 10:
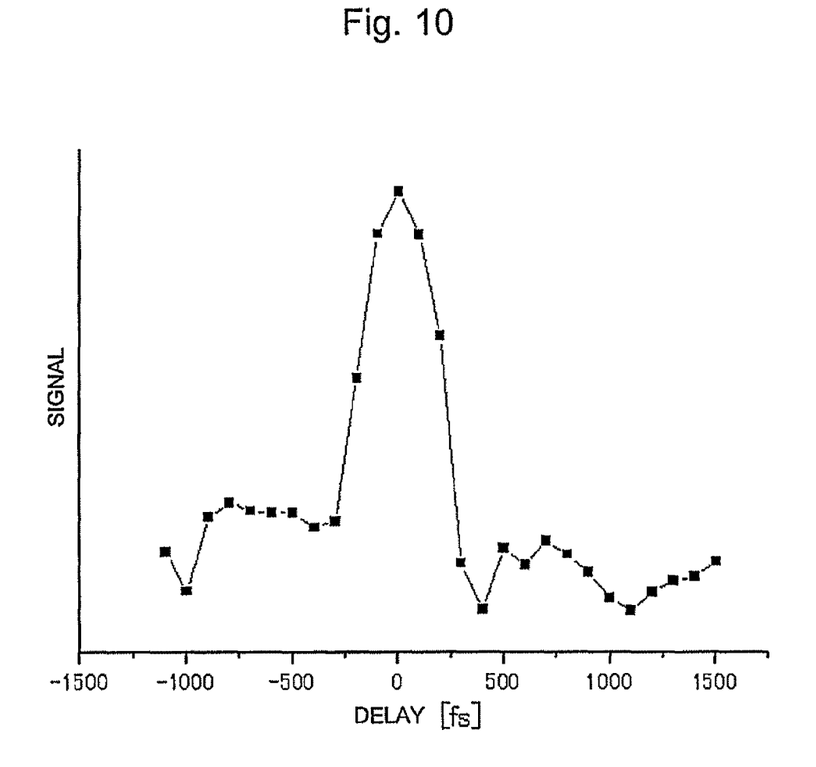
FIG. 10 is a graph showing the cross-correlation function of the electron pulse and laser pulse measured with the time width measurement device.

Subsequently, the time width of the electron pulse was measured which was delivered onto the sample to be measured by the aforementioned device. FIG. 9 shows the configuration of the device used. This device is different from the device of FIG. 5 in that the time width of the electron pulse at the position of the sample was determined by means of a cross-correlation method using a ponderomotive scattering (Christoph T. Hebeisen et al., Optics Letters, 31, 3517 (2006)). That is, the sample to be measured was removed and electron lenses were provided before and after the position of the sample. The anterior electron lens converges an electron beam to approximately 20 μm at the position of the sample, and a laser pulse (which has the same characteristics of those of the aforementioned pulse for generating electrons) was laterally delivered thereto. The electron beam effected by the laser pulse is projected onto the screen by the rear electron lens. The timing of the laser pulse emission was altered by a 100 fs increment to observe the change of the spatial distribution of the electron beam on the screen, and thereby the cross-correlation function between the electron pulse and the laser pulse was obtained. FIG. 10 shows the result. The correlation width demonstrates that the time width of the electron pulse was not more than 500 fs.

Figure 11A:
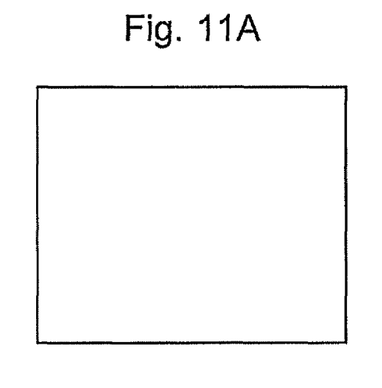
FIGS. 11A and 11B are respectively a front view and a sectional view of an intensity-gradient magnetostatic field forming device.
Figure 11B:
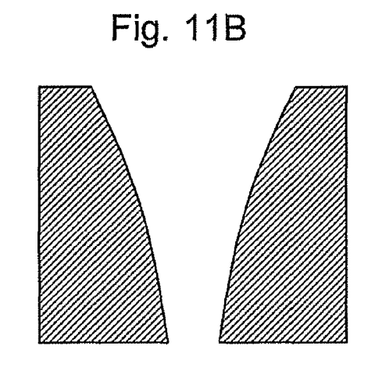
Figure 11C:
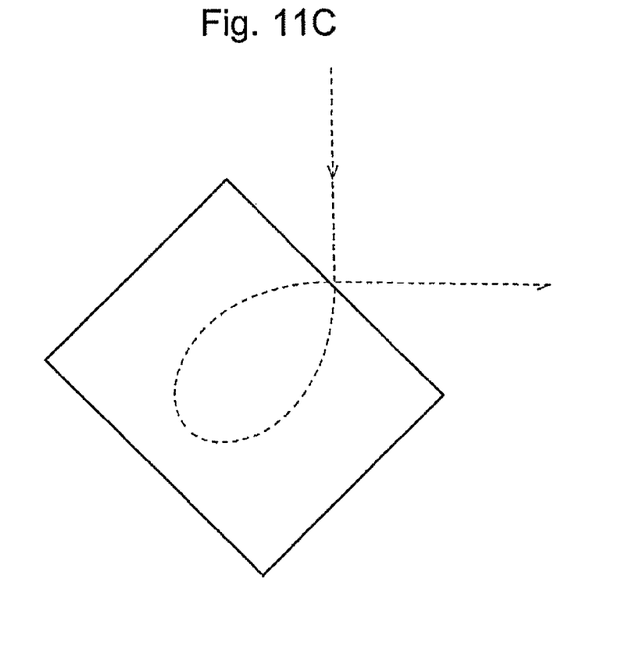
FIG. 11C shows a path of an electron beam.

A conventional intensity-gradient magnetostatic field (refer to Non-Patent document 2, for example) may be used as the pulse compressor of the present invention. FIGS. 11A through 11C show an example. This device is composed of a pair of planer magnets as shown in FIG. 11A. As shown in FIG. 11B, the distance between the inner sides (i.e. the flight space of an electron beam) of the two magnets gradually decreases, thereby gradually changing the magnetic field in the flight space. When an electron beam is injected into this device, its spread in the z-direction can be suppressed at approximately 270°, as shown in FIG. 11C.

INDUSTRIAL APPLICABILITY

The ultrafast electron diffraction device according to the present invention enables an ultrafast observation of a phenomenon which changes in femtoseconds. Such an observation can be practically applied not only to the study of physical reaction or fast chemical reaction of a substance, but also to the materials science or biology. For example, the observation of a phase change of a metallic material when a high-intensity laser is delivered thereon enables a precise condition setting for a surface treatment.

In the aforementioned example, the state change was observed in the sample when it was induced by light as a pump. However, the present method can be extended to an excitation other than light. That is, if the light used as a pump is delivered at a higher intensity to a different target, radiation such as a short pulse X-ray, electron beam, or ion beam, or a white light can be generated. By delivering such radiation as a pump onto a sample to be measured, its state change after that can be observed. This can be put to use, for example, in understanding the process of radiation damage to material used in such devices as atomic reactors. Biological tissues, cells and the like can be spectrographically excited by a white light.

The invention claimed is:

1. An ultrafast electron diffraction device for irradiating a sample with a bunch of electrons in an ultrashort time pulse in order to perform an ultrafast analysis of the sample, comprising:
   a) a laser emitter for delivering an ultrashort pulse laser having a pulse width of not more than 1 ps onto a target which is a material for generating electrons at an intensity of not less than $10^{17}$ W/cm$^2$; and
   b) a pulse compressor for rotating, in a magnetostatic field, a bunch of electrons generated from the target onto which the ultrashort pulse laser has been delivered so as to suppress a spread of the bunch of electrons in their travelling direction,
   wherein the pulse compressor comprises an entrance-side parallel-plate static magnet and an exit-side parallel plate static magnet which is tilted vertically to the entrance-side parallel plate static magnet.

2. The ultrafast electron diffraction device according to claim 1, further comprising a sample exciter for exciting the sample.

3. The ultrafast electron diffraction device according to claim 1, wherein the pulse compressor uses an intensity-gradient magnetostatic field.

4. An ultrafast electron diffraction method comprising:
   a) a laser emission step for delivering an ultrashort pulse laser having a pulse width of not more than 1 ps onto a target at an intensity of not less than $10^{17}$ W/cm$^2$;

b) a pulse compression step for rotating, in a magnetostatic field, a bunch of electrons generated from the target onto which the ultrashort pulse laser has been delivered so as to suppress a spread of the bunch of electrons in their travelling direction; and c) a sample irradiation step for delivering the bunch of electrons whose spread in the travelling direction has been suppressed onto a sample, wherein, in the pulse compression step, a pulse compressor comprising an entrance-side parallel-plate static magnet and an exit-side parallel plate static magnet which is tilted vertically to the entrance-side parallel plate static magnet is used.

5. The ultrafast electron diffraction method according to claim 4, wherein the sample is excited in the sample irradiation step.

6. The ultrafast electron diffraction method according to claim 4, wherein an intensity-gradient magnetostatic field is used in the pulse compression step.

7. The ultrafast electron diffraction device according to claim 2, wherein the pulse compressor uses an intensity-gradient magnetostatic field.

8. The ultrafast electron diffraction method according to claim 5, wherein an intensity-gradient magnetostatic field is used in the pulse compression step.

9. An ultrafast electron diffraction device for irradiating a sample with a bunch of electrons in an ultrashort time pulse in order to perform an ultrafast analysis of the sample, comprising:

a pulse compressor for rotating, in a magnetostatic field, a bunch of electrons generated from a target onto which an ultrashort pulse laser has been delivered so as to suppress a spread of the bunch of electrons in their travelling direction, wherein the pulse compressor comprises an entrance-side parallel-plate static magnet and an exit-side parallel plate static magnet which is tilted vertically to the entrance-side parallel plate static magnet.

\* \* \* \* \*